United States Patent
Wakita et al.

(10) Patent No.: US 8,518,994 B2
(45) Date of Patent: Aug. 27, 2013

(54) ARGININE DERIVATIVE AND COSMETIC CONTAINING THE SAME

(75) Inventors: Kazuaki Wakita, Kanagawa (JP); Susumu Tanaka, Kanagawa (JP); Kei-ichi Maruyama, Kanagawa (JP)

(73) Assignee: NOF Corporation, Tokyo (JP)

( * ) Notice: Subject to any disclaimer, the term of this patent is extended or adjusted under 35 U.S.C. 154(b) by 65 days.

(21) Appl. No.: 13/140,468

(22) PCT Filed: Dec. 25, 2009

(86) PCT No.: PCT/JP2009/071687
§ 371 (c)(1),
(2), (4) Date: Jun. 17, 2011

(87) PCT Pub. No.: WO2010/074268
PCT Pub. Date: Jul. 1, 2010

(65) Prior Publication Data
US 2011/0245344 A1 Oct. 6, 2011

(30) Foreign Application Priority Data
Dec. 26, 2008 (JP) .................................. 2008-331874

(51) Int. Cl.
| A61K 8/44 | (2006.01) |
| C07C 279/14 | (2006.01) |
| C07C 277/08 | (2006.01) |
| A61Q 19/00 | (2006.01) |

(52) U.S. Cl.
USPC .......................................... 514/565; 562/560

(58) Field of Classification Search
None
See application file for complete search history.

(56) References Cited

U.S. PATENT DOCUMENTS
| 4,032,676 A | 6/1977 | Heins et al. |
| 5,089,605 A * | 2/1992 | Profy et al. ................ 530/388.1 |
| 5,100,655 A | 3/1992 | Takano et al. |
| 5,919,748 A | 7/1999 | Noguchi et al. |
| 2006/0018864 A1 | 1/2006 | Yoshioka et al. |

FOREIGN PATENT DOCUMENTS
| CN | 1161958 A | 10/1997 |
| CN | 1406123 A | 3/2003 |
| EP | 0282308 A2 | 9/1988 |
| EP | 0830856 A1 | 3/1998 |
| EP | 1 210 933 A1 | 6/2002 |
| EP | 1 325 735 A2 | 7/2003 |
| EP | 1584320 A1 | 10/2005 |
| JP | 48-022417 A | 3/1973 |
| JP | 50-095201 A | 7/1975 |
| JP | 63-258500 A | 10/1988 |
| JP | 02-000764 A | 1/1990 |
| JP | 09-271655 A | 10/1997 |
| JP | 2008143839 A | 6/2008 |
| WO | 2004/052318 A1 | 6/2004 |

OTHER PUBLICATIONS
Extended European Search Report 09835604.8 issued Jun. 13, 2012.
International Search Report (PCT/ISA/210), dated Jan. 26, 2010, issued in Application No. PCT/JP2009/071687.
International Written Opinion (PCT/ISA/237), dated Jan. 26, 2010, issued in Application No. PCT/JP2009/071687.
Office Action dated Mar. 5, 2013 issued by the State Intellectual Property Office of P.R. China in corresponding Chinese Patent Application No. 200980151406.7.
Search Report dated Jan. 23, 2013, issued by the Intellectual Property Office of Singapore in Singaporean Application No. 201104657-0.
Written Opinion dated Jan. 23, 2013, issued by the Intellectual Property Office of Singapore in Singaporean Application No. 201104657-0.

* cited by examiner

*Primary Examiner* — Dennis Heyer
(74) *Attorney, Agent, or Firm* — Sughrue Mion, PLLC

(57) ABSTRACT

An object of the invention is to provide a novel arginine derivative and a cosmetic satisfactory in compatibility with the skin and hair, excellent in skin softening effect and skin-conditioning effect, and satisfactory in use feeling with little sticky feeling and tense feeling.
Such present invention relates to an arginine derivative represented by the following general formula (1):

$$
\underset{R^2}{\overset{R^1}{\underset{|}{N}}}\!\!-\!\!\overset{}{\underset{\underset{O}{\parallel}}{C}}\!\!-\!\!\overset{OR^3}{\underset{}{}}\cdots\overset{NH_2}{\underset{}{}}\cdots\overset{H}{\underset{N}{}}\!\!-\!\!\overset{NH}{\underset{}{}}\quad(1)
$$

wherein $R^1$ and $R^2$ are a hydrogen atom or a linear or branched monohydroxyalkyl group having 2 to 3 carbon atoms and at least one of $R^1$ and $R^2$ represents a linear or branched monohydroxyalkyl group having 2 to 3 carbon atoms; and $R^3$ represents a hydrogen atom, an alkali metal atom, an ammonium, or an organic ammonium, and a cosmetic containing the same mixed therein.

3 Claims, No Drawings

ARGININE DERIVATIVE AND COSMETIC CONTAINING THE SAME

TECHNICAL FIELD

The present invention relates to a novel arginine derivative and a process for producing the same. More particularly, it relates to a cosmetic containing a novel arginine derivative.

BACKGROUND ART

Amino acids have been widely used as cosmetic raw materials as materials excellent in biocompatibility and environmental compatibility, and many attempts at derivatization have been made with aiming at further functionalization. Among major amino acids, arginine has a guanidinyl group as a characteristic functional group in the molecule and is excellent in absorbability to the skin and hair, so that various arginine derivatives have been developed. For example, Patent Document 1 reports a higher alkyl (12 to 22 carbon atoms) ester salt of N-long chain acyl (8 to 22 carbon atoms) arginine and a hair cosmetic containing the same.

Moreover, Patent Document 2 reports an N-long chain (4 to 30 carbon atoms) alkylamino acid derivative characterized by reacting 1,2-epoxyalkane having 4 to 30 carbon atoms with an alkaline metal salt or an amino acid whose carboxyl group is protected through esterification, in an alcohol or a mixed solvent of an alcohol and water.

However, the arginine derivative or N-long chain (4 to 30 carbon atoms) alkylamino acid derivative is a surfactant and may sometimes generate a tense feeling and a rough feeling, so that the amount thereof to be added to cosmetics is limited.

On the other hand, Patent Document 3 reports an arginine N-glyceryl derivative (N-(2,3-dihydroxypropyl)-L-arginine) obtained by reacting arginine with glycidol or 3-halo-1,2-propanediol. However, the arginine N-glyceryl derivative has a high moisturizing property as compared with arginine and does not generate a tense feeling and a rough feeling, but it is not sufficiently satisfactory from the viewpoints of compatibility with the skin and hair, softening of the skin, and a skin conditioning effect.

Furthermore, from the viewpoint of a production method, since a large amount of an organic solvent is required for solubilizing an acyl halide compound having 8 to 22 carbon atoms or a higher alcohol having 12 to 22 carbon atoms in the production process of Patent Document 1 and a 1,2-epoxyalkane having 4 to 30 carbon atoms in the production process of Patent Document 2 at the reaction, environmental burden is large and there is a concern about a residual solvent in the case of the use as a cosmetic base material. In the production process of Patent Document 3, for activating the α-amino group of the amino acid, pH is adjusted to 8 to 11 with an alkali agent or an acid agent. However, in the case where the amino acid and glycidol or 3-halo-1,2-propanediol are reacted in the presence of an alkali metal or the like, impurity in association with side reactions are generated, so that deterioration of a use feeling by the influence of the impurities is a problem in the case of the use as cosmetics.

BACKGROUND ART DOCUMENTS

Patent Documents

Patent Document 1: Japan: JP-A-2-764
Patent Document 2: Japan: JP-A-48-22417
Patent Document 3: pamphlet of International Publication No. 2004-052318

SUMMARY OF THE INVENTION

Problems that the Invention is to Solve

An object of the invention is to provide a novel arginine derivative and a cosmetic satisfactory in compatibility with the skin and hair, excellent in skin softening effect and skin-conditioning effect, and satisfactory in use feeling with little sticky feeling and tense feeling. Furthermore, it is to provide a production process which suppresses the generation of impurities resulting from side reactions.

Means for Solving the Problems

Namely, the invention relates to the following.
(1) An arginine derivative represented by the following general formula (1):

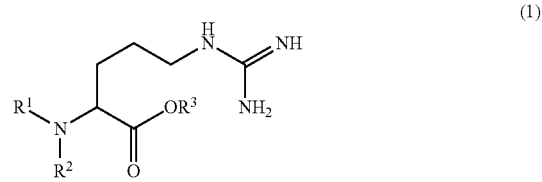

wherein $R^1$ and $R^2$ are a hydrogen atom or a linear or branched monohydroxyalkyl group having 2 to 3 carbon atoms and at least one of $R^1$ and $R^2$ represents a linear or branched monohydroxyalkyl group having 2 to 3 carbon atoms; and $R^3$ represents a hydrogen atom, an alkali metal atom, an ammonium, or an organic ammonium.

(2) A cosmetic containing the arginine derivative according to the above (1) mixed therein.

(3) A process for producing an arginine derivative represented by the following general formula (1):

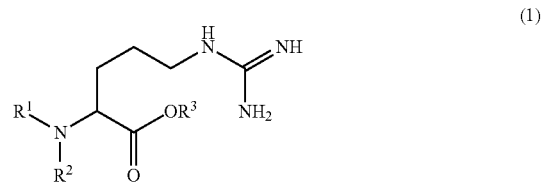

wherein $R^1$ and $R^2$ are a hydrogen atom or a linear or branched monohydroxyalkyl group having 2 to 3 carbon atoms and at least one of $R^1$ and $R^2$ represents a linear or branched monohydroxyalkyl group having 2 to 3 carbon atoms; and $R^3$ represents a hydrogen atom, an alkali metal atom, an ammonium, or an organic ammonium, which comprises dissolving arginine into water and reacting it without any catalyst at the time when an alkylene oxide having 2 to 3 carbon atoms is added.

Advantage of the Invention

The arginine derivative of the invention is suitably used for cosmetics and the cosmetics are satisfactory in compatibility with the skin and hair, excellent in skin softening effect and skin-conditioning effect, and satisfactory in use feeling with little sticky feeling and tense feeling. Furthermore, the generation of impurities resulting from side reactions can be suppressed by the production process of the invention.

MODE FOR CARRYING OUT THE INVENTION

The following will describe the invention in detail.

In the arginine derivative represented by the formula (1), $R^1$ and $R^2$ are a hydrogen atom or a linear or branched monohydroxyalkyl group having 2 to 3 carbon atoms, which specifically includes a monohydroxyethyl group and a monohydroxypropyl group. The monohydroxypropyl group is more preferred for the compatibility with the skin and hair and the skin softening effect, and the monohydroxyethyl group is preferred for the skin-conditioning effect. In the case where alkyl chain length of the monohydroxyalkyl group exceeds 3, there is a case where surface activation ability is expressed and causes a tense feeling.

The arginine derivative of the invention includes a one-mol adduct wherein either of $R^1$ and $R^2$ is a monohydroxyalkyl group and a two-mol adduct wherein both of $R^1$ and $R^2$ are a monohydroxyalkyl group. The number of mol added can be controlled by a charging ratio of ethylene oxide or propylene oxide to arginine. In view of excellence in the compatibility with the skin and hair, the skin softening effect, and the skin-conditioning effect, the two-mol added body is more preferred.

Arginine as a starting material, all of a D isomer, an L isomer and a DL isomer can be used but an L isomer is preferred in view of general availability.

In the formula (1), $R^3$ represents a hydrogen atom, an alkali metal atom, an ammonium, or an organic ammonium. Examples of the alkali metal atom include sodium, potassium, lithium, and the like. The ammonium is a group represented by the formula $NH_4^+$. Moreover, the organic ammonium is a group represented by the formula $NR_4^+$, wherein R represents a hydrogen atom or an alkyl group such as methyl or ethyl or an alkyl group where a part of hydrogen atoms is replaced by the other group(s) and at least one of the R groups is not a hydrogen atom.

$R^3$ other than a hydrogen atom can be introduced by allowing a base such as an alkali metal hydroxide, ammonia, or an organic amine to act on the arginine derivative represented by the formula (1).

However, when the above base is allowed to act before the reaction of arginine with an alkylene oxide, side reactions of the alkylene oxide are promoted and impurities are prone to be formed. Therefore, in the case of introducing $R^3$, it is preferred to allow the base to act on the arginine derivative represented by the formula (1).

The arginine derivative of the invention can be obtained by reacting arginine with ethylene oxide or propylene oxide using water as a solvent. Also, after the arginine derivative represented by the formula (1) is obtained, it may be transformed into an acid addition salt with an acid agent. Examples of the acid addition salt include organic acid salts having 6 or less carbon atoms, such as acetate salts, lactate salts, glycolate salts, glutamate salts, aspartate salts, pyridinecarboxylate salts, citrate salts, malate salts, tartrate salts, succinate salts, and adipate salts, and inorganic acid salts such as hydrochloride salts, sulfate salts, and phosphate salts.

The reaction of arginine with ethylene oxide or propylene oxide for obtaining the arginine derivative represented by the formula (1) can be carried out in an aqueous solution without any catalyst. Specifically, the arginine derivative represented by the formula (1) is obtained by preparing an aqueous arginine solution having a prescribed concentration and carrying out the reaction under heating without adjusting pH while adding ethylene oxide or propylene oxide dropwise under stirring. An acid addition salt of the arginine derivative is obtained by pH adjustment with an acid agent.

At the reaction, a water-soluble organic solvent such as an alcohol can be also used but since ethylene oxide or propylene oxide are arbitrarily soluble with water, the reaction proceeds with no trouble even when no water-soluble organic solvent is used. Moreover, when a possibility of occurrence of a side reaction of an alcohol with the alkylene oxide, a risk of a residual solvent, burden on the environment, and the like are considered, it is preferred to use water as a solvent without using the water-soluble organic solvent.

Since arginine is a strongly basic amino acid, an aqueous solution thereof shows a basic character. Therefore, the α-amino group is activated without adding an alkali agent and reacts with ethylene oxide or propylene oxide. On the other hand, in the case where an alkali metal or alkaline earth metal derived from the alkali agent is present, the alkali metal or alkaline earth metal acts as a catalyst for the reaction of the alkylene oxide with water, so that impurities such as glycols are prone to be formed. Therefore, the reaction is preferably carried out without any catalyst.

The reaction temperature is preferably from 30 to 90° C., more preferably from 40 to 80° C., and further preferably from 45 to 70° C. When the reaction temperature is lower than 30°, the reaction rate decreases and when the reaction temperature is higher than 90° C., generation of an odor and coloration are prone to occur.

The time for dropwise addition of ethylene oxide or propylene oxide at the reaction varies depending on the quantity to be reacted but, for completing the reaction after the dropwise addition is finished, it is preferred to continue stirring for 3 to 10 hours under heating.

In the case of synthesizing the one-mol adduct, since the reaction proceeds almost quantitatively, excess ethylene oxide or propylene oxide is unnecessary. However, in the case of synthesizing the two-mol adduct, the reactivity of a secondary amino group decreases as compared with a primary amino group, excess ethylene oxide or propylene oxide is necessary. The excess amount is from 1.1 to 1.4 times and more preferably from 1.2 to 1.3 times based on the necessary number of mol added.

It is also a characteristic feature of the process for producing the arginine derivative of the invention that unreacted ethylene oxide or propylene oxide can be easily removed by an operation such as bubbling with nitrogen after the completion of the reaction. It is also possible to use the resulting arginine derivative as an aqueous solution or to use it as a powder after a treatment such as spray drying.

As cosmetics of the invention, those used for the outer skin (inclusive of scalp) and the hair as cosmetics, medicaments, or medicated cosmetics are exemplified as representatives thereof. Specific examples thereof include facial cosmetics such as face lotions, emulsions, creams, and packs, make-up cosmetics such as foundation, lipsticks, and eye shadow, body cosmetics such as body soap and body creams, pretreating agents and post-treating agents for hair dyeing, hair cosmetics such as shampoos, hair rinses, hair conditioners, hair creams, hair dyes, and split end coatings, and the like.

The content of the arginine derivative represented by the formula (1) in the cosmetics of the invention varies depending on the kind of the cosmetics but is preferably from 0.05 to 30% by mass and more preferably from 0.1 to 20% by mass. When the content is less than 0.05% by mass, the compatibility with the skin, the softening and skin-conditioning effect, a hair-strengthening effect on the hair, and the like are not obtained in some cases. On the other hand, when the content exceeds 30% by weight, there is a concern that a trouble may take place at the formulation and stickiness may be generated on the skin or hair.

Into the cosmetics of the invention, in addition to the arginine derivative of the formula (1), ingredients for use in usual cosmetics, e.g., oily materials, moisturizing agents, surfactants, thickeners, antioxidants, UV absorbents, chelating agents, perfumes, animal/plant extracts, and the like can be suitably mixed.

The form of the cosmetics of the invention is arbitrary and any of solution type, solubilized type, emulsion type, gel type, powder-dispersed type, water-oil bilayer type, and the other type ones is possible. They can be produced by mixing the arginine derivative represented by the above formula (1) with the above optional mixing ingredients according to objective products.

EXAMPLES

The following will describe the invention in further detail with reference to Examples.
<Analytical Conditions>
$^1$H-NMR: For nuclear magnetic resonance spectroscopy (NMR), ECP-400 (400 MHz) manufactured by JOEL Ltd. was employed. From the ratio of peak area of the hydrogen atoms appearing at 1.5 to 1.7 ppm and bonded to β-carbon and γ-carbon of arginine to peak area of the hydrogen atoms appearing at around 3.8 ppm and bonded to the carbon atom at 2-position of the 2-hydroxyalkyl group, the number of the 2-hydroxyalkyl groups introduced into the α-amino group was calculated.

(Number of 2-hydroxyalkyl groups introduced into α-amino group)=(Peak area of hydrogen atoms bonded to carbon atom at 2-position of 2-hydroxyalkyl groups)/(Peak area of hydrogen atoms bonded to β-carbon and γ-carbon of L-arginine)×4

Incidentally, each arginine derivative was freeze-dried and used as a measuring sample. Capillary electrophoresis (CP): As a capillary electrophoresis apparatus, CAPI3330 manufactured by Otsuka Electronics Co. Ltd. was used and measurement was performed for each sample under the following conditions.

Sample introduction method: the sample was collected by a head drop method (25 mm, 120 seconds) (utilizing the siphon principle)
Measuring wavelength: 210 nm (indirect UV method)
Applied voltage: +25 kV (migrated at a constant voltage)
Migration fluid: 10 mM imidazole (fluorescent agent), 2 mM 18-crown ether (chelating agent), 5 mM 2-hydroxybutyric acid, 5 mM citric acid monohydrate (buffer agent)
Sample concentration: 50 ppm
Measuring temperature: 25° C.
Capillary: a silica-made hollow capillary having an inner diameter of 75 μm and a total length of 800 mm was used
Incidentally, each arginine derivative was freeze-dried and used as a measuring sample.

Synthetic Example of Compound 1

Synthesis of 30% by Mass Aqueous N-(2-hydroxyethyl)-L-Arginine Solution

First, 174 g (1 mol) of L-arginine was dissolved into 406 g of ion-exchange water and charged into an autoclave and the air in the autoclave was replaced by dry nitrogen. Then, the autoclave was heated to 60° C. and 44 g (1 mol) of ethylene oxide was gradually added dropwise through a dropping apparatus over a period of 1 hour. After the dropwise addition was finished, the whole was further stirred for 6 hours. After the reaction was finished, bubbling with dry nitrogen was performed for 30 minutes to remove unreacted ethylene oxide and the reaction composition was taken out of the autoclave.

A part of the reaction composition was taken out, moisture was removed by freeze-drying, and the resulting one was used as a sample for analysis. Based on $^1$H-NMR spectra, the 2-hydroxyethyl group introduced into the α-amino group was found to be 1.02 mol. Moreover, based on the analysis by the capillary electrophoresis (CP), a main peak was confirmed at a retention time of 8 minutes and, in addition, a minute amount of the other ingredients were contained. Based on the analytical results obtained by $^1$H-NMR and CP, the main ingredient was judged to be N-(2-hydroxyethyl)-L-arginine.

Ion-exchange water was added to the reaction product taken out of the autoclave so that the solid mass concentration became 30% by mass, thereby preparing a 30% by mass aqueous N-(2-hydroxyethyl)-L-arginine solution, which was used in the following investigation.

Synthetic Example of Compound 2

Synthesis of 30% by Mass Aqueous N,N-bis(2-hydroxyethyl)-L-Arginine Solution

First, 174 g (1 mol) of L-arginine was dissolved into 406 g of ion-exchange water and charged into an autoclave and the air in the autoclave was replaced by dry nitrogen. Then, the autoclave was heated to 60° C. and 88 g (2 mol) of ethylene oxide was gradually added dropwise through a dropping apparatus over a period of 1 hour. After the dropwise addition was finished, the whole was further stirred for 6 hours. After the reaction was finished, bubbling with dry nitrogen was performed for 30 minutes to remove unreacted ethylene oxide and the reaction composition was taken out of the autoclave.

A part of the reaction composition was taken out, moisture was removed by freeze-drying, and the resulting one was used as a sample for analysis. Based on $^1$H-NMR spectra, the 2-hydroxyethyl group introduced into the α-amino group was found to be 1.98 mol. Moreover, based on the analysis by the capillary electrophoresis (CP), a main peak was confirmed at a retention time of 8 minutes and 30 seconds and, in addition, a minute amount of the other ingredients were contained. Based on the analytical results obtained by $^1$H-NMR and CP, the main ingredient was judged to be N,N-bis(2-hydroxyethyl)-L-arginine.

Ion-exchange water was added to the reaction product taken out of the autoclave so that the solid mass concentration became 30% by mass, thereby preparing a 30% by mass aqueous N,N-bis(2-hydroxyethyl)-L-arginine solution, which was used in the following investigation.

Synthetic Example of Compound 3

Synthesis of 30% by Mass Aqueous N-(2-hydroxypropyl)-L-Arginine Solution

First, 174 g (1 mol) of L-arginine was dissolved into 406 g of ion-exchange water and charged into an autoclave and the air in the autoclave was replaced by dry nitrogen. Then, the autoclave was heated to 60° C. and 58 g (1 mol) of propylene oxide was gradually added dropwise through a dropping apparatus over a period of 1 hour. After the dropwise addition was finished, the whole was further stirred for 6 hours. After the reaction was finished, bubbling with dry nitrogen was performed for 30 minutes to remove unreacted propylene oxide and the reaction composition was taken out of the autoclave.

A part of the reaction composition was taken out, moisture was removed by freeze-drying, and the resulting one was used as a sample for analysis. Based on $^1$H-NMR spectra, the 2-hydroxypropyl group introduced into the α-amino group was found to be 1.04 mol. Moreover, based on the analysis by the capillary electrophoresis (CP), a main peak was confirmed at a retention time of 8 minutes and 10 seconds and, in addition, a minute amount of the other ingredients were contained. Based on the analytical results obtained by $^1$H-NMR and CP, the main ingredient was judged to be N-(2-hydroxypropyl)-L-arginine.

Ion-exchange water was added to the reaction product taken out of the autoclave so that the solid mass concentration became 30% by mass, thereby preparing a 30% by mass aqueous N-(2-hydroxypropyl)-L-arginine solution, which was used in the following investigation.

Synthetic Example of Compound 4

Synthesis of 30% by Mass Aqueous N,N-bis(2-hydroxypropyl)-L-Arginine Solution

First, 174 g (1 mol) of L-arginine was dissolved into 406 g of ion-exchange water and charged into an autoclave and the air in the autoclave was replaced by dry nitrogen. Then, the autoclave was heated to 60° C. and 116 g (2 mol) of propylene oxide was gradually added dropwise through a dropping apparatus over a period of 1 hour. After the dropwise addition was finished, the whole was further stirred for 6 hours. After the reaction was finished, bubbling with dry nitrogen was performed for 30 minutes to remove unreacted propylene oxide and the reaction composition was taken out of the autoclave.

A part of the reaction composition was taken out, moisture was removed by freeze-drying, and the resulting one was used as a sample for analysis. Based on $^1$H-NMR spectra, the 2-hydroxypropyl group introduced into the α-amino group was found to be 1.94 mol. Moreover, based on the analysis by the capillary electrophoresis (CP), a main peak was confirmed at a retention time of 8 minutes and 40 seconds and, in addition, a minute amount of the other ingredients were contained. Based on the analytical results obtained by $^1$H-NMR and CP, the main ingredient was judged to be N,N-bis(2-hydroxyprolyl)-L-arginine.

Ion-exchange water was added to the reaction product taken out of the autoclave so that the solid mass concentration became 30% by mass, thereby preparing a 30% by mass aqueous N,N-bis(2-hydroxypropyl)-L-arginine solution, which was used in the following investigation.

Synthetic Example of Compound 5

Synthesis of 30% by Mass Aqueous N-(2,3-dihydroxypropyl)-L-Arginine Solution

First, 174 g (1 mol) of L-arginine was dissolved into 406 g of ion-exchange water and charged into an autoclave and the air in the autoclave was replaced by dry nitrogen. Then, the autoclave was heated to 60° C. and 74 g of glycidol was gradually added dropwise through a dropping apparatus over a period of 1 hour. After the dropwise addition was finished, the whole was further stirred for 6 hours. After the reaction was finished, bubbling with dry nitrogen was performed for 30 minutes and the reaction composition was taken out of the autoclave.

A part of the reaction composition was taken out, moisture was removed by freeze-drying, and the resulting one was used as a sample for analysis. Based on $^1$H-NMR spectra, the 2,3-dihydroxypropyl group introduced into the α-amino group was found to be 0.94 mol. Moreover, based on the analysis by the capillary electrophoresis (CP), a main peak was confirmed at a retention time of 7 minutes and 50 seconds and, in addition, a minute amount of the other ingredients were contained. Based on the analytical results obtained by $^1$H-NMR and CP, the main ingredient was judged to be N-(2, 3-dihydroxypropyl)-L-arginine.

Ion-exchange water was added to the reaction product taken out of the autoclave so that the solid mass concentration became 30% by mass, thereby preparing a 30% by mass aqueous N-(2,3-dihydroxypropyl)-L-arginine solution, which was used in the following investigation.

Synthetic Example of Compound 6

Synthesis of 30% by Mass Aqueous N-(2-hydroxybutyl)-L-Arginine Solution

First, 174 g (1 mol) of L-arginine was dissolved into 203 g of ion-exchange water and 203 g of 2-propanol and charged into an autoclave and the air in the autoclave was replaced by dry nitrogen. Then, the autoclave was heated to 80° C. and 72 g (1 mol) of butylene oxide was gradually added dropwise through a dropping apparatus over a period of 1 hour. After the dropwise addition was finished, the whole was further stirred for 6 hours. After the reaction was finished, the reaction composition was taken out of the autoclave. 2-Propanol and water was removed therefrom by distillation on a rotary evaporator and the residue was dried under vacuum to obtain a reaction product as a white solid.

Based on $^1$H-NMR spectra, the 2-hydroxybutyl group introduced into the α-amino group was found to be 0.97 mol. Moreover, based on the analysis by the capillary electrophoresis (CP), a main peak was confirmed at a retention time of 9 minutes and 10 seconds and, in addition, a minute amount of the other ingredients were contained. Based on the analytical results obtained by $^1$H-NMR and CP, the main ingredient was judged to be N-(2-hydroxybutyl)-L-arginine.

Ion-exchange water was added to the reaction product taken out of the autoclave so that the solid mass concentration became 30% by mass, thereby preparing a 30% by mass aqueous N-(2-hydroxybutyl)-L-arginine solution, which was used in the following investigation.

Synthetic Example of Compound 7

Synthesis of 30% by Mass Aqueous N-(2-hydroxydodecyl)-L-Arginine Solution

First, 174 g (1 mol) of L-arginine was dissolved into 348 g of ion-exchange water and 348 g of 2-propanol and charged into an autoclave and the air in the autoclave was replaced by dry nitrogen. Then, the autoclave was heated to 80° C. and 184 g (1 mol) of dodecylene oxide (1,2-epoxydodecane) was gradually added dropwise through a dropping apparatus over a period of 1 hour. After the dropwise addition was finished, the whole was further stirred for 6 hours. After the reaction was finished, the reaction composition was taken out of the autoclave. 2-Propanol and water was removed therefrom by distillation on a rotary evaporator and the residue was dried under vacuum to obtain a reaction product as a white solid.

Based on $^1$H-NMR spectra, the 2-hydroxydodecyl group introduced into the α-amino group was found to be 0.94 mol. Moreover, based on the analysis by the capillary electrophoresis (CP), a main peak was confirmed at a retention time of 9 minutes and 30 seconds and, in addition, a minute amount of the other ingredients were contained. Based on the analytical results obtained by $^1$H-NMR and CP, the main ingredient was judged to be N-(2-hydroxydodecyl)-L-arginine.

Ion-exchange water was added to the reaction product taken out of the autoclave so that the solid mass concentration became 30% by mass, thereby preparing a 30% by mass aqueous N-(2-hydroxydodecyl)-L-arginine solution, which was used in the following investigation.

Examples 1 to 5 and Comparative Examples 1 to 5

As shown in Table 1, Compounds 1 to 4 as the arginine derivatives of the invention, Compounds 5 to 7 and arginine as comparative ingredients, and ingredients shown in Table 2 as common additive ingredients were selected and skin lotions were prepared. In this regard, the lotions were adjusted to have pH of 6.0 to 7.0 with L-glutamic acid and citric acid and then were used for the following use feeling tests.

<Evaluation Method>

A. Regarding "Compatibility with Skin"

A use-feeling test was performed by 20 expert panelists. Regarding the compatibility with the skin at the time when 0.5 mL of each skin lotion was applied onto back of the hand, each panelist evaluated the lotion as four grades with reference to the following absolute evaluation and scored. Then, the scores given by all panelists were summed up on each sample and those scored 30 points or more was regarded as being passed. However, in the case where 3 or more panelists scored a sample 0 point, the sample was regarded as being rejected.

<Absolute Evaluation Criteria>

(Score): (Evaluation)
- 3: Compatibility with the skin is satisfactory
- 2: Compatibility with the skin is slightly satisfactory
- 1: Compatibility with the skin is slightly poor
- 0: Compatibility with the skin is poor B. Regarding "Skin Softening Effect"

A use-feeling test was performed by 20 expert panelists. Namely, 0.5 mL of each skin lotion was applied onto back of the hand. Regarding the skin softening effect after 2 hours from the application, each panelist evaluated the lotion as four grades with reference to the following absolute evaluation and scored. Then, the scores given by all panelists were summed up on each sample and those scored 30 points or more was regarded as being passed. However, in the case where 3 or more panelists scored a sample 0 point, the sample was regarded as being rejected.

<Absolute Evaluation Criteria>

(Score): (Evaluation)
- 3: Puffy flexibility is felt on the skin after application
- 2: Puffy flexibility is slightly felt on the skin after application
- 1: Puffy flexibility is not much felt on the skin after application
- 0: Puffy flexibility is not felt at all on the skin after application C. Regarding "Sticky Feeling"

A use-feeling test was performed by 20 expert panelists. Regarding the sticky feeling at the time when 0.5 mL of each skin lotion was applied onto back of the hand, each panelist evaluated the lotion as four grades with reference to the following absolute evaluation and scored. Then, the scores given by all panelists were summed up on each sample and those scored 30 points or more was regarded as being passed. However, in the case where 3 or more panelists scored a sample 0 point, the sample was regarded as being rejected.

<Absolute Evaluation Criteria>

(Score): (Evaluation)
- 3: Stickiness is hardly felt on the skin after application
- 2: Stickiness is not much felt on the skin after application
- 1: Stickiness is slightly felt on the skin after application
- 0: Stickiness is felt on the skin after application D. Regarding "Skin-Conditioning Effect"

A long-term successive use test was performed by 20 male panelists. Namely, 0.5 mL of each skin lotion was applied onto an inner part of the forearm in the morning and evening twice per day over a period of two weeks. After two weeks, the skin texture conditions were observed by a microscope and a expert evaluator evaluated the lotion as four grades with reference to the following absolute evaluation and scored. Then, the scores were summed up on each sample and those scored 30 points or more was regarded as being passed.

<Absolute Evaluation Criteria>

(Score): (Evaluation)
- 3: Skin grooves are clear and homogeneous and an improvement is observed as compared with those before the test
- 2: With regard to clarity and homogeneity of skin grooves, a slight improvement is observed as compared with those before the test
- 1: With regard to clarity and homogeneity of skin grooves, a slight deterioration is observed as compared with those before the test
- 0: Skin grooves are unclear and heterogeneous (anisotropic character increases) and a deterioration is observed as compared with those before the test E. Regarding "Tense Feeling"

A use-feeling test was performed by 20 expert panelists. After face washing, each skin lotion was applied onto the face. Thereafter, regarding the tense feeling within 2 hours after application, each panelist evaluated the lotion as four grades with reference to the following absolute evaluation and scored. Then, the scores given by all panelists were summed up on each sample and those scored 30 points or more was regarded as being passed. However, in the case where 3 or more panelists scored a sample 0 point, the sample was regarded as being rejected.

<Absolute Evaluation Criteria>

(Score): (Evaluation)
- 3: After application, no tense feeling was felt within 2 hours
- 2: After application, a slight tense feeling was felt within 2 hours
- 1: After application, a tense feeling was felt within 2 hours
- 0: After application, a strong tense feeling was felt within 2 hours

TABLE 1

| | | % by weight | | | | | | | | |
|---|---|---|---|---|---|---|---|---|---|---|
| | | Example | | | | | Comparative Example | | | |
| | Compound | 1 | 2 | 3 | 4 | 5 | 1 | 2 | 3 | 4 |
| | Compound 1 | — | 10.0 | | | | | | | |
| | Compound 2 | | | 10.0 | | | | | | |
| | Compound 3 | | | | 10.0 | | | | | |
| | Compound 4 | 10.0 | | | | 10.0 | | | | |
| Comparative Ingredient | Compound 5 | | | | | | 10.0 | | | |
| | Compound 6 | | | | | | | 10.0 | | |
| | Compound 7 | | | | | | | | 10.0 | |
| | L-Arginine | | | | | | | | | 10.0 |
| | L-Glutamic acid (pH adjustor) | appropriate amount* | — | — | — | — | — | — | — | — |
| | Citric acid (pH adjustor) | — | | | | appropriate amount* | | | | |
| | Common additive ingredient | 7.0 | | | | | | | | |
| | Water | remainder | | | | | | | | |
| Evaluation | Compatibility with skin | 55 | 46 | 49 | 54 | 56 | 24 | 49 | 40 | 15 |
| | Softening effect | 56 | 45 | 48 | 53 | 55 | 26 | 43 | 28 | 18 |
| | Sticky feeling | 49 | 48 | 44 | 52 | 50 | 28 | 44 | 31 | 50 |
| | Skin-conditioning effect | 45 | 53 | 56 | 40 | 44 | 38 | 22 | 12 | 20 |
| | Tense feeling | 58 | 57 | 55 | 58 | 59 | 49 | 27 | 19 | 55 |

*pH of the formulation was adjusted to 6.0 to 7.0.

TABLE 2

| Common Additive Ingredient | Mixing ratio (% by weight) |
|---|---|
| Glycerin | 2.0 |
| Dipropylene glycol | 3.0 |
| Polyethylene glycol 1540 | 1.0 |
| Urea | 0.5 |
| Antiseptic | 0.5 |
| Total | 7.0 |

From Examples 1 to 5, the cosmetics containing the arginine derivative of the invention are satisfactory in compatibility with the skin and hair, excellent in skin softening effect and skin conditioning effect, and satisfactory in use feeling with little sticky feeling and tense feeling in all the samples.

On the other hand, sufficient effects are not obtained in Comparative Examples 1 to 4. In Comparative Example 1, since $R^1$ or $R^2$ is a 2,3-dihydroxypropyl group derived from arginine and glycidol, the compatibility with the skin, the skin softening effect, and the sticky feeling after application are insufficient. In Comparative Example 2, since the monohydroxyalkyl group has 4 carbon atoms, the skin-conditioning effect is insufficient and the tense feeling is felt after application. In Comparative Example 3, since the monohydroxyalkyl group has 12 carbon atoms, the skin-conditioning effect and the softening effect are insufficient and the tense feeling is felt after application. In comparative Example 4, owing to unmodified L-arginine, the compatibility with the skin, the softening effect, and the skin-conditioning effect are insufficient.

While the invention has been described in detail and with reference to specific embodiments thereof, it will be apparent to one skilled in the art that various changes and modifications can be made therein without departing from the spirit and scope thereof.

The present application is based on Japanese Patent Application No. 2008-331874 filed on Dec. 26, 2008, and the whole contents are incorporated herein by reference. Also, all the references cited herein are incorporated as a whole.

The invention claimed is:

1. An arginine derivative represented by the following general formula (I):

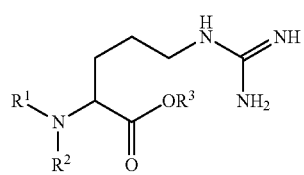

(1)

wherein $R^1$ and $R^2$ are a linear or branched monohydroxyalkyl group having 2 to 3 carbon atoms; and $R^3$ represents a hydrogen atom, an alkali metal atom, an ammonium, or an organic ammonium.

2. A cosmetic comprising the arginine derivative as claimed in claim 1 mixed therein.

3. A process for producing an arginine derivative represented by the following general formula (I):

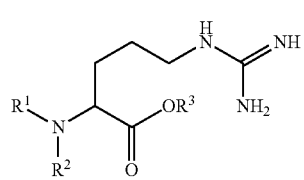

(1)

wherein $R^1$ and $R^2$ are a linear or branched monohydroxyalkyl group having 2 to 3 carbon atoms; and $R^3$ represents a hydrogen atom, an alkali metal atom, an ammonium, or an organic ammonium, which process comprises dissolving arginine into water and reacting it without any catalyst at the time when an alkylene oxide having 2 to 3 carbon atoms is added.

* * * * *